United States Patent [19]

Bienhaus et al.

[11] Patent Number: 5,576,219
[45] Date of Patent: Nov. 19, 1996

[54] STANDARD SOLUTIONS FOR DETERMINATION OF THYROXINE-BINDING CAPACITY IN SERUM

[75] Inventors: Gerhard Bienhaus, Wörthesee; Helmut Jering, Tutzing, both of Germany

[73] Assignee: Boehringer Mannheim GmbH, Mannheim-Waldhof, Germany

[21] Appl. No.: 190,705

[22] Filed: Feb. 2, 1994

Related U.S. Application Data

[63] Continuation of Ser. No. 869,905, Apr. 15, 1992, abandoned, which is a continuation of Ser. No. 334,675, Apr. 6, 1989, abandoned.

[30] Foreign Application Priority Data

Apr. 15, 1988 [DE] Germany ............... 38 12 610.9

[51] Int. Cl.⁶ .................................................. G01N 33/78
[52] U.S. Cl. .................... 436/500; 435/7.9; 435/7.92; 435/7.93; 435/967
[58] Field of Search .................. 436/500, 8, 16, 436/808, 815; 435/7.9, 7.92, 7.93, 967, 975

[56] References Cited

U.S. PATENT DOCUMENTS

| | | | |
|---|---|---|---|
| 4,052,504 | 10/1977 | Hertl et al. | |
| 4,391,795 | 7/1983 | Pearlman | 436/500 |
| 4,438,202 | 3/1984 | Engler et al. | 436/8 |
| 4,467,030 | 8/1984 | Kleinhammer et al. | 435/7.93 |
| 4,476,228 | 10/1984 | Huchzermeier et al. | 436/500 |
| 4,678,754 | 7/1987 | Hoskins | 436/15 |
| 4,786,591 | 11/1988 | Draeger et al. | |
| 4,824,777 | 4/1989 | Chang et al. | 435/7.92 |
| 5,342,788 | 8/1994 | Kunst et al. | 436/500 |

FOREIGN PATENT DOCUMENTS

| | | |
|---|---|---|
| 0298708 | 1/1989 | European Pat. Off. . |
| 3504406 | 8/1986 | Germany . |

OTHER PUBLICATIONS

Clinical Chemistry, vol. 32, Nr. 5, 1986, pp. 826–830; H. R. Schroeder et al, "Homogeneous Apoenzyme Reactivation Immunoassay for Thyroxin–Binding Globulin in Serum".

Sigma Chemical Company Catalogue. pp. 306, 1268–1269, (1987).

Kilduff et al, J. Endocor. 107:383–387 (1985).

*Primary Examiner*—Mary E. Ceperley
*Attorney, Agent, or Firm*—Felfe & Lynch

[57] ABSTRACT

The present invention provides a process for the determination of the thyroxine-binding capacity in serum, wherein, for the calibration, there are used at least two different standard solutions which contain substantially the same amount of thyroxine-binding globulin but a differing content of thyroxine.

The present invention also provides a standard solution for the determination of the thyroxine-binding capacity containing thyroxine-binding globulin dissolved in a buffer system.

8 Claims, 3 Drawing Sheets

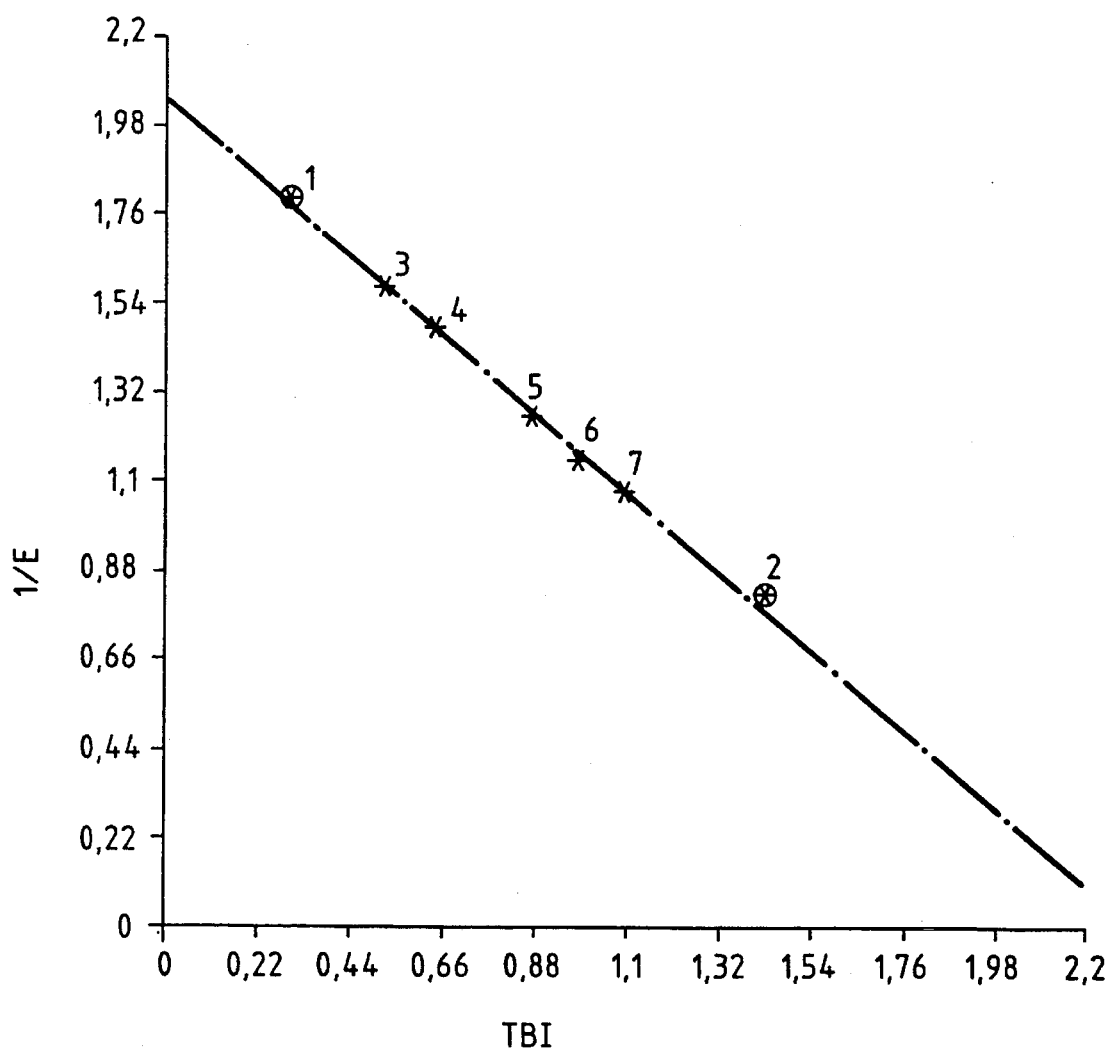

STANDARD SOLUTIONS FOR DETERMINATION OF THYROXINE-BINDING CAPACITY IN SERUM

This application is a continuation of application Ser. No. 07/869,905, filed Apr. 15, 1992 now, abandoned which is a continuation of application Ser. No. 07/334,675 filed Apr. 6, 1989, now abandoned.

The present invention is concerned with a process for the determination of the thyroxine-binding capacity in serum.

In the case of the determination of the thyroxine-binding capacity, which is also called the "uptake test", there is determined the residual binding capacity of carrier proteins for thyroid hormones in the sera of patients. The thyroid hormones are present in the blood substantially in protein-bound form. The most important carrier protein is thereby thyroxine-binding globulin, which is called TBG and is bound to about 80% of the thyroxine present in the blood. About 5 to 10% of the total thyroxine is present bound to albumin and about 10 to 15% of the total thyroxine is present bound to pre-albumin. The totality of these proteins is also called thyroxine-binding protein (TBP). Only a very small proportion of the thyroxine is present in the blood in free form this being, as a rule, about 0.03%. Only the free thyroxine is physiologically effective, whereas the bound thyroxine circulates in the blood as a metabolically inert transport form and serves as buffer for the regulation of the level of the free thyroxine. Therefore, it is important to determine not only the total thyroxine content and the proportion of free thyroxine in the blood but also the transport capacity of the TBP since only in conjunction with this value can a diagnosis be made with regard to the function of the thyroid gland.

Various processes according to the immunoassay principle are known for the determination of the residual binding capacity of the TBP.

In the case of a process known from European Patent Specification No. 0,006,998, to a serum sample to be investigated are added labelled thyroxine ($T_4$), immobilised anti-$T_4$-antibody and a known amount of thyroxine which is greater than the amount which can still be bound by the TBP. The non-bound added thyroxine and the labelled thyroxine then compete for the anti-$T_4$-antibody. From the amount of labelled $T_4$ bound to the antibody there can then be deduced the amount of thyroxine bound to the TBP and thus the binding capacity can be determined in an indirect way.

In the case of another known process described in European Patent Specification No. 0,108,400 U.S. Pat. No. 4,476,228, in homogeneous phase there is added fluorescence-labelled $T_4$ which can bind to TBP. The change of the fluorescence polarisation taking place by this binding is then a measure for the thyroxine binding capacity.

In the case of yet another process for the determination of the thyroxine binding capacity which is described in European Patent Specification No.0,006,998, (U.S. Pat. No. 4,476,030 issued Aug. 21, 1984) a definite amount of radioactive triiodothyronine ($T_3$) is mixed with the serum sample and an anion exchanger. The free binding points of the carrier protein and of the anion exchanger compete for the radioactive $T_3$. The more unoccupied binding places are present on the carrier protein, the more radioactive $T_3$ is there bound, the remainder going to the ion exchanger. The evaluation takes place by measuring either the radio-activity on the ion exchanger or in the solution. The ratio of the radioactivity in the solution, which corresponds to that amount of radioactive $T_3$ which is bound to the carrier proteins of the serum to be investigated, to the radioactivity in the solution of a standard sample multiplied by a factor specific for the standard gives the so-called thyroxine binding index TBI.

A further possibility is described in Federal Republic of Germany Patent Specifications Nos. 35 04 406 and 35 46 014 (U.S. Pat. No. 4,786,591 issued Nov. 22, 1981). In this case, to the sample solution is added an insufficiency of labelled $T_4$ or $T_3$ and immobilised anti-$T_4$ or -TBG antibody. The difference between the amount of added labelled $T_3$ and $T_4$ and the labelled $T_3$ and $T_4$ bound to the solid phase then gives the binding capacity of TBP.

For all of these processes, it is necessary to have available standard solutions with known binding capacity for the calibration. A problem thereby arises since, on the one hand, the standard solution should have substantially the same composition as the solution to be measured, i.e. the serum, and, on the other hand, only a known amount of TBP should be present in the standard solution. For the calibration, it is thereby necessary to have available at least two standard solutions with different thyroxine-binding capacities. For the preparation of standard solutions, serum can, for example, be freed from TBG by known processes and then made up with purified TBG. This process is very laborious and, furthermore, has the disadvantage that the mixing of two different standard solutions for the production of intermediate standard solutions does not give a linear calibration line so that it is not possible to produce a calibration curve by two-point standardisation.

Therefore, it is an object of the present invention to provide standard solutions for the determination of the binding capacity of TBP which are simple to produce, give good recovery rates and make possible a linear calibration curve so that two measurements are sufficient for the standardisation.

Thus, according to the present invention, there is provided a process for the determination of the thyroxine-binding capacity in serum, wherein, for the calibration, there are used at least two different standard solutions which substantially contain the same amount of TBG but have a different thyroxine content.

Surprisingly, we have ascertained that very precise values are obtained when, as standard solutions, solutions are used in which the TBG content is constant but in which the thyroxine content is different. Thus, whereas hitherto the possibilities of solving the production of standard solutions was sought exclusively in a variation of the TBG content of the solutions, it has now been found that a variation of the thyroxine content gives more precise and more linear curves.

In the meaning of the present invention, by thyroxine there is also to be understood triiodothyronine.

The preparation of the standard solutions can take place starting from human serum, serum being used which is thyroxine-free. Thyroxine-free human serum can be obtained by bringing the serum into contact with preferably immobilised anti-thyroxine antibodies for a sufficiently long period of time. These thyroxine-free solutions can then be mixed with a definite amount of TBG, whereby a thyroxine-free solution can be used as a first standard solution and one made up with thyroxine as a second standard solution.

However, it is also possible to use standard solutions which contain TBG, albumin and a buffer system. We have, surprisingly, ascertained that such synthetically produced standard solutions also give outstanding recovery values. These solutions are easy to prepare and, on the basis of the definite components which they contain, are very stable and can, therefore, be kept for a comparatively long period of time.

The standard solutions preferably used for the process according to the present invention contain, as important component, thyroxine-binding globulin (TBG). TBG can be obtained from human sera in known manner. The standard solutions used according to the present invention preferably contain 10 to 80 µg./ml. TBG and especially preferably 30 to 40 µg./ml.

Furthermore, the standard solutions used according to the present invention preferably contain albumin. Albumin stabilises the solutions and thus makes possible longer storage times. For this purpose, it is not necessary to use human serum albumin as albumin although this is, of course, also suitable. It is also possible to use the overall easily obtainable and substantially more favourable albumins from bovine or horse serum. As albumin, it is preferred to use human serum albumin, bovine serum albumin or horse serum albumin, bovine serum albumin being especially preferred. The albumin is preferably used in an amount of from 40 to 80 mg./ml. and especially preferably in a physiological amount.

The components TBG and possibly albumin are dissolved in a buffer system. As buffer systems, there can be used all buffers which have a pH range of from 6 to 8 and preferably of from 6.5 to 7.5, those with a pH value of 7.0 being especially preferred. There is preferably used a phosphate buffer or a GOOD buffer, for example HEPES or TRIS buffer. The buffer concentration is not critical but the buffer is preferably used in a concentration of from 30 to 150 mM/liter. Especially preferably, the standard solutions contain 50 to 100 mM/liter of buffer.

The solution prepared by dissolving TBG and possibly albumin in buffer can then be used as first standard solution. For the preparation of further standard solutions with differing thyroxine content, the thyroxine can be added to this solution in appropriate concentrations. As a rule, in the case of the use of two standard solutions for the production of a calibration curve, there is used a solution with a lower concentration of thyroxine and a solution with a higher concentration of thyroxine, whereby in the first solution there is then available a higher percentage of free binding points of the TBPs for the binding of the thyroxine, whereas in the latter solution there is only present a smaller percentage of binding points for the thyroxine. The solution with higher binding capacity preferably contains up to 25 ng./ml. thyroxine. It can also be thyroxine-free. The solution with a lower binding capacity preferably contains 250 to 500 ng./ml. thyroxine and especially preferably 300 to 350 ng./ml. There is thereby then adjusted an equilibrium between protein-bound and free thyroxine, analogous to the equilibrium prevailing in vivo in the blood. On the basis of their composition, these solutions are also stable for a comparatively long period of time. Since they are prepared from standardised individual substances, they always display a uniform composition and, therefore, provide reproducible values.

The present invention also provides standard solutions for the determination of the thyroxine-binding capacity which contain TBG dissolved in a buffer system.

The standard solutions differ by the content of thyroxine. The thyroxine content of the solution is adjusted by the addition of a definite amount of thyroxine.

The standard solution preferably contains 10 to 80 µg./ml. of TBG, more preferably 20 to 50 µg./ml. of TBG and especially preferably physiological amounts of TBG.

The buffer system preferably has a pH value in the range of from 6 to 8 and more preferably of from 6.5 to 7.5 and is preferably a GOOD buffer or phosphate buffer.

For increasing the stability, the standard solution preferably also contains albumin, preferably in the range of from 40 to 80 ng./ml. albumin.

Furthermore, according to the present invention, there is also provided a standard combination for the determination of the thyroxine-binding capacity which consists of two solutions physically separated from one another, one of which contains 10 to 80 µg./ml. of TBG and 20 to 800 ng./ml. thyroxine dissolved in a buffer system and the other of which contains 10 to 80 µg./ml. of TBG dissolved in a buffer system.

The standard solutions can be prepared, for example, by dissolving physiological amounts of TBG and possibly of albumin in a buffer system and adding the particularly desired amount of thyroxine.

According to the present invention, standard solutions with superior stability are made available which can be prepared in a simple manner from easily obtainable starting materials. Furthermore, the calibration values obtained with the standard solutions according to the present invention give linear curves so that the determination of two standard values suffice for the standardisation of the determination.

The following Examples are given for the purpose of illustrating the present invention with reference to the accompanying drawings, in which:

FIG. 3 shows a calibration curve which has been produced with standard solutions according to the present invention based on a buffer solution with different $T_4$ concentrations.

EXAMPLE 1

Standard solutions were prepared as are described in the prior art.

Standard solution 1 contains TBG-free serum made up with 3.75 µg. TBG/ml.;

Standard solution 2 contains TBG-free serum made up with 150 µg. TBG/ml.

Figure 1:
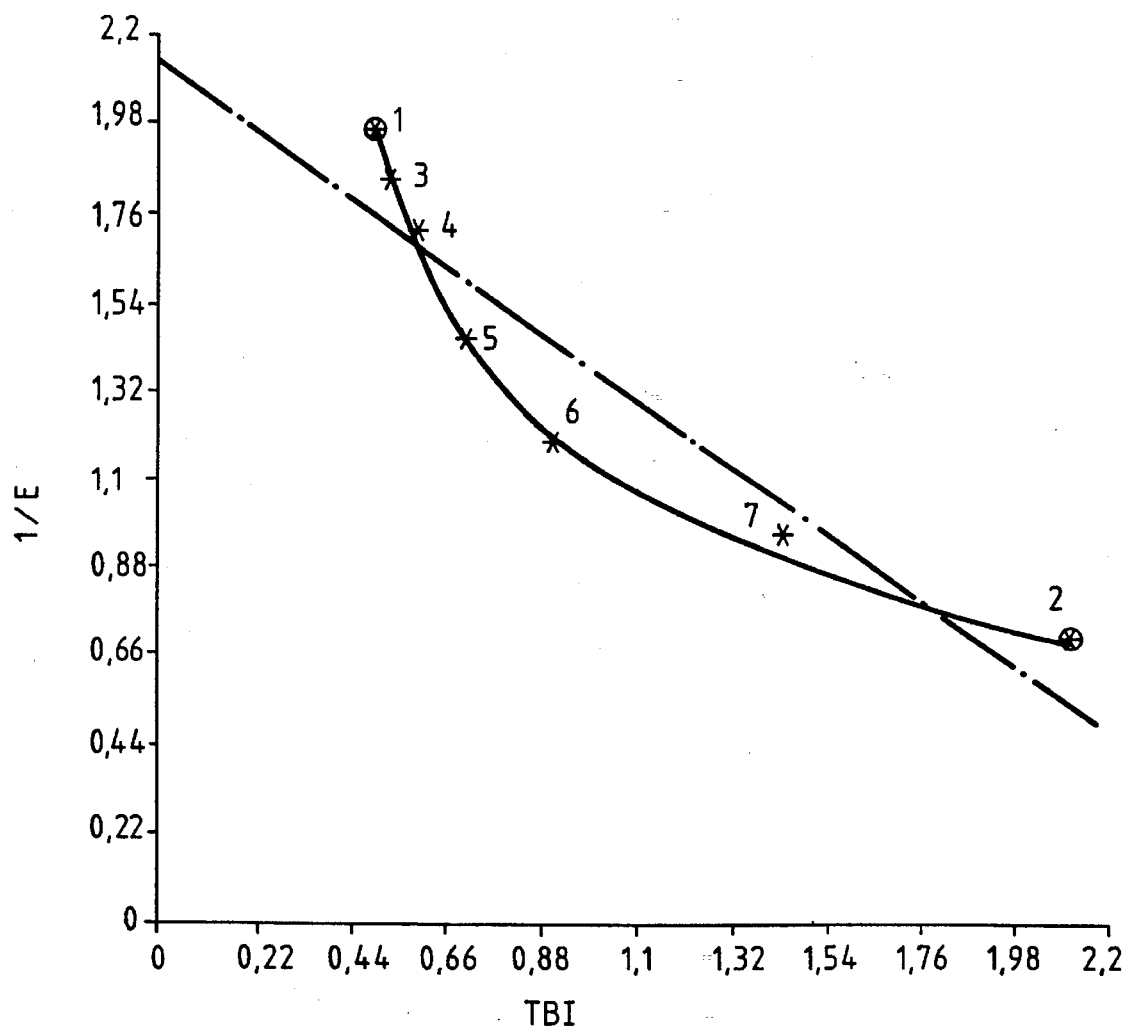
FIG. 1 shows a calibration curve which has been produced with standard solutions according to the prior art for the determination of the thyroxine-binding capacity.

With these two standard solutions, there were prepared further intermediate standards 3 to 7 (cf. FIG. 1):

| intermediate standard | standard soln. 1 vol. parts | standard soln. 2 vol. parts |
|---|---|---|
| 3 | 9 | 1 |
| 4 | 8 | 2 |
| 5 | 6 | 4 |
| 6 | 4 | 6 |
| 7 | 2 | 8 |

The TBG determination took place as described in Example 2. For the evaluation, the reciprocal extinction (1/E) was plotted against the thyroxine-binding index (TBI).

EXAMPLE 2

A standard solution according to the present invention was prepared on the basis of a human serum matrix. For this purpose, on to BrCN-Sephadex were coupled purified antibodies against thyroxine from sheep, which had been obtained according to the method of K. Heide et al., "Handbook of Experimental Immunology", Vol. 1, 2nd ed. (1973 ), D. M. Weir, pub. Oxford Blackwell Scientific, 6.1–7.16, according to the method of Fuchs et al., "Handbook of Experimental Immunology", Vol. 1, 2nd ed. (1973), D. M. Weir, pub. Oxford Blackwell Scientific, 11.1–11.4. In this way, there was obtained an immunoadsorber with sufficient thyroxine-binding capacity. 6 liters of sterile filtered human serum were then pumped over the immunoadsorber at 37° C. which had previously been equilibrated with 0.9% aqueous sodium chloride solution. Subsequently, washing was carried out with 1 liter of 0.9% aqueous sodium chloride solution. The eluate was collected directly in ice-cooled receivers, pooled and sterile filtered. The thyroxine content of the solution obtained was determined with the help of an enzyme immunoassay. It was less than 20 ng. $T_4$/ml.

The so obtained substantially thyroxine-free human serum solution was then made up with TBG. For this purpose, lyophilised TBG was used which had been prepared as described by B. Kagedahl et al., Clinical Clinica Acta, 78, 103–111/1977. The TBG was dissolved with a concentration of 1 mg. TBG/ml. in the $T_4$-impoverished human serum. With this TBG solution was prepared, by mixing with the $T_4$-impoverished human serum, a dilution series with solutions which contained 0, 5, 10, 20, 40, 50 and 100 mg. TBG/liter. The thyroxine binding was determined in these solutions with an enzyme immunoassay as described in European Patent Specification No 0,006,998. For this purpose, into glass test tubes coated with anti-$T_4$ antibody were pipetted 10 μl. of serum and subsequently 1 ml. of a reagent which contained 280 ng $T_4$/ml. and 10 mU/ml. $T_4$-POD in 0.12M barbital buffer (pH 8.6) and 0.2% bovine serum albumin. The mixture was then left to stand for 2 hours at ambient temperature. Thereafter, the test tubes were sucked empty and a POD reagent introduced. The latter consisted of 1.47 mM/liter hydrogen peroxide and 14 mM/liter ABTS (diammonium salt of 2,2'-azino-di-[3-ethylbenzthiazolin-6-sulphonic acid]) in 0.2M phosphate-citrate buffer (pH 5.0). The colour change which occurred was measured at 405 nm.

From the values obtained is given the amount of TBG with which the $T_4$-impoverished human serum must be made up in order to produce a measurement signal which corresponds to the desired value for the highest thyroxine-binding capacity. In the present example, this amount was 15 mg. TBG/liter, which gave a thyroxine-binding index value (TBI value) of 1.39.

To the so prepared solution (first standard solution or 1 standard solution), which contained a known amount of TBG, was added L-thyroxine in various concentrations. For this purpose, L-thyroxine was dissolved in a little sodium hydroxide and ethanol and diluted in $T_4$-impoverished human serum to a solution with a concentration of 1 mg. $T_4$/ml. From this solution was prepared a dilution series, solutions thereby being obtained which contained 0, 300, 400, 500 and 600 ng. $T_4$/ml. The thyroxine-binding capacity of these solutions was again determined. That solution, the measurement signal of which corresponded to the desired low thyroxine-binding capacity, was further used as the second standard solution or standard solution 2. The so made up serum was stirred for 1 hour at ambient temperature in order to bring about a complete adjustment of the equilibrium.

In the present example, the standard solution with 420 ng. $T_4$/ml. proved to be suitable as the second standard solution or standard solution 2. This corresponds to a TBI value of 0.11.

Figure 2:
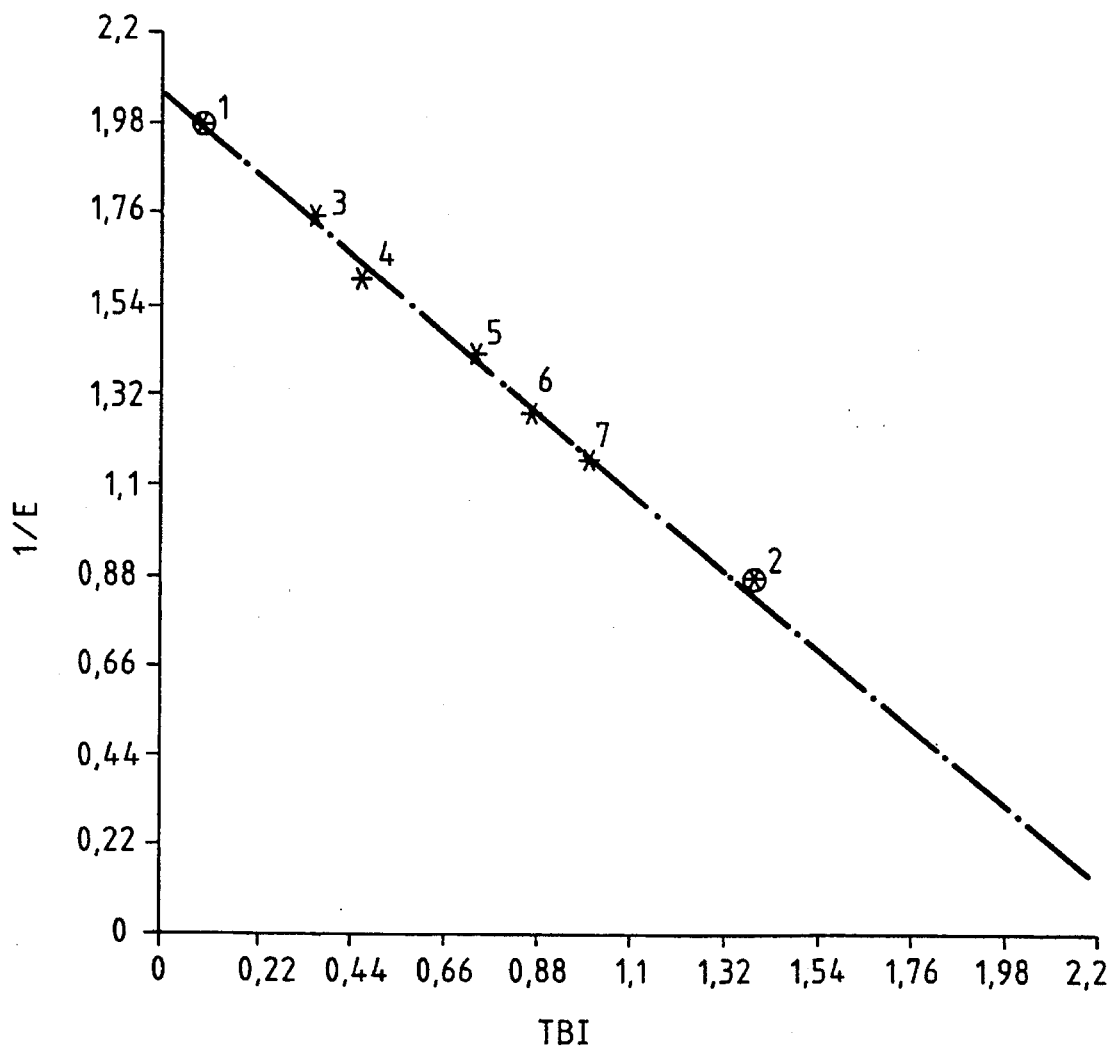
FIG. 2 shows a calibration curve which has been produced with standard solutions according to the present invention based on human serum with different $T_4$ concentrations.

A calibration curve was then produced with the so prepared standard solutions. For this purpose, various mixtures of the two standard solutions 1 and 2 were prepared and designated with 3 to 7 as in FIG. 2 of the accompanying drawings. These standard solutions were prepared as follows:

| standard | parts by vol. of 1 | parts by vol. of 2 |
| --- | --- | --- |
| 3 | 8 | 2 |
| 4 | 7 | 3 |
| 5 | 5 | 5 |
| 6 | 4 | 6 |
| 7 | 3 | 7 |

The thyroxine-binding capacity of the solutions was then determined as described above. To the mixtures were then assigned the calculated TBI values. These calculated TBI values were then plotted against the reciprocal measurement values of the extinction (1/E). The results are to be seen from FIG. 2 of the accompanying drawings.

The correlation coefficients of a linear regression analysis were:

R=0.9989 for the standard solutions according to the invention (FIG. 2) and

R=0.9349 for standard solutions according to the prior art.

EXAMPLE 3

A first standard solution was prepared. For this purpose, lyophilised TBG which had been prepared as described in Example 2, in phosphate buffer, which consisted of 50 mM/liter monosodium dihydrogen phosphate, 60 mg./ml. bovine serum albumin, 0.1% Tween 20 and 0.9% sodium chloride adjusted with sodium hydroxide to pH 7.4, was dissolved with a concentration of 1 mg. TBG/ml. From this solution was prepared a dilution series with phosphate buffer. For the individual solutions, there was determined the thyroxine-binding capacity value (TBC value) as described in Example 2. A first standard solution or standard solution 1 contained 48 mg. TBG/liter. This gave a measurement signal which corresponded to a TBI serum value of 1.43.

A $T_4$ solution was prepared as described in Example 2, L-thyroxine thereby being dissolved in phosphate buffer instead of in human serum. The dilution series was prepared with standard solution 2. Then, as described in Example 2, the TBC value was determined for the various solutions. As the second standard solution standard solution 2, there was used a solution which contained 420 ng. $T_4$/ml. This standard solution could be associated with a TBC value of 0.32.

From the two standard solutions 1 and 2 were again prepared mixtures (designated in FIG. 3 of the accompanying drawing with 3 to 7) and the TBK values of these mixtures determined.

The standard solutions 3 to 7 were prepared as follows:

| standard | parts by volume of 1 | parts by volume of 2 |
| --- | --- | --- |
| 3 | 8 | 2 |
| 4 | 7 | 3 |
| 5 | 5 | 5 |
| 6 | 4 | 6 |
| 7 | 3 | 7 |

The thyroxine-binding capacity was determined as in Example 2 and the reciprocal extinction (1/E) plotted against TBI.

There was again obtained a linear curve, the correlation coefficient of which to the linear regression analysis gave 0.9974 (see FIG. 3).

It will be understood that the specification and examples are illustrative but not limitative of the present invention and that other embodiments within the spirit and scope of the invention will suggest themselves to those skilled in the art.

We claim:

1. In a reagent kit for the determination of thyroxine binding capacity in serum wherein the kit contains reagents effective for the determination of thyroxine binding protein comprising components selected from the group consisting of antibodies against thyroxine, labeled antibodies against thyroxine, thyroxine, labeled thyroxine, effective buffers, effective standards, and detection reagents the improvement consisting of two separate serum-free standard solutions, the first standard solution containing 10 to 60 µg/ml thyroxine-binding globulin and 100–500 ng/ml thyroxine dissolved in a buffer system having a pH range of 6 to 8 together with 40–80 mg/ml albumin and the second standard solution containing 10 to 60 µg/ml thyroxine-binding globulin dissolved in a buffer system having a pH range of 6 to 8 together with 40–80 mg/ml albumin.

2. In a process for the determination of thyroxine-binding capacity in serum wherein a characteristic related to the capacity is determined by effective methods of determination, the improvement consisting essentially of calibrating said effective determination by means of two different serum-free standard solutions wherein a first standard solution contains a buffer system having a pH range of 6–8, 40–80 mg/ml albumin, 10 to 60 µg/ml thyroxine-binding globulin thereby corresponding to the highest thyroxine-binding capacity of human serum and a second standard solution contains a buffer system having a pH rang of 6–8, 40–80 mg/ml albumin, 10 to 60 µg/ml thyroxine-binding globulin and 100–500 ng/ml thyroxine thereby corresponding to the lowest thyroxine-binding capacity of human serum and adding each standard to a separate container having T4 antibody, further adding a predetermined amount of a reagent containing T4 and enzyme-conjugated T4 to each container, incubating the containers to permit competitive binding of the T4 and enzyme-conjugated T4 to thyroxine-binding protein and the anti-T4, removing unbound immunoreactants, adding substrate for the enzyme, determining, the amount of enzyme bound by measuring the colored product formed to produce a calibration curve from the values as determined above for the two standards, and determining the amount of thyroxine-binding capacity by the effective method for determination with reference to the above calibration curve.

3. The process of claim 2 wherein said albumin is human serum albumin, bovine serum albumin or horse serum albumin.

4. The process of claim 3 wherein said albumin is bovine serum albumin.

5. The process of claim 2 wherein the buffer is a phosphate or a GOOD buffer.

6. The process of claim 5 wherein the GOOD buffer is a HEPES or a TRIS buffer.

7. In a process for the determination of thyroxine-binding capacity in serum wherein a characteristic related to the capacity is determined by effective methods of determination, the improvement consisting essentially of calibrating the determination by means of two different serum-free standard solutions wherein a first standard solution contains a buffer system having a pH range of 6–8, a physiological amount of albumin, 10 to 60 µg/ml thyroxine-binding globulin thereby corresponding to the highest thyroxine-binding capacity of human serum and a second standard solution contains a buffer system having a pH rang of 6–8, a physiological amount of albumin, 10 to 60 µg/ml thyroxine-binding globulin and 100–500 ng/ml thyroxine thereby corresponding to the lowest thyroxine-binding capacity of human serum and adding each standard to a separate container having T4 antibody, further adding a predetermined amount of a reagent containing T4 and enzyme-conjugated T4 to each container, incubating the containers to permit competitive binding of the T4 and enzyme-conjugated T4 to thyroxine-binding protein and the anti-T4, removing unbound immunoreactants, adding substrate for the enzyme, determining, the amount of enzyme bound by measuring the colored product formed to produce a calibration curve from the values as determined above for the two standards, determining the amount of thyroxine-binding capacity by the effective method for determination with reference to the aforesaid calibration curve.

8. The process of claim 7 wherein said standard solutions contain bovine serum albumin.

* * * * *